(12) United States Patent
Tsai et al.

(10) Patent No.: US 12,331,131 B2
(45) Date of Patent: Jun. 17, 2025

(54) PERSONALIZED CANCER IMMUNOTHERAPY

(71) Applicant: NAVI BIO-THERAPEUTICS, INC., Kaohsiung (TW)

(72) Inventors: Bor-Yu Tsai, New Taipei (TW); Kuang-Yu Chen, Kaohsiung (TW); Shin-Tsung Huang, Taipei (TW); Wei-Ting Hsu, Taipei (TW)

(73) Assignee: NAVI BIO-THERAPEUTICS, INC., Kaohsiung (TW)

( * ) Notice: Subject to any disclaimer, the term of this patent is extended or adjusted under 35 U.S.C. 154(b) by 423 days.

(21) Appl. No.: 17/027,419

(22) Filed: Sep. 21, 2020

(65) Prior Publication Data
US 2021/0101993 A1 Apr. 8, 2021

Related U.S. Application Data

(60) Provisional application No. 62/903,416, filed on Sep. 20, 2019.

(51) Int. Cl.
| | | |
|---|---|---|
| C07K 16/00 | (2006.01) | |
| C07K 16/30 | (2006.01) | |
| G01N 33/574 | (2006.01) | |

(52) U.S. Cl.
CPC ............ *C07K 16/30* (2013.01); *C07K 16/005* (2013.01); *G01N 33/57407* (2013.01); *C07K 2317/565* (2013.01); *G01N 2333/988* (2013.01)

(58) Field of Classification Search
CPC .................. C07K 16/30; C07K 16/005; C07K 2317/565; G01N 33/57407; G01N 2333/988
See application file for complete search history.

(56) References Cited

U.S. PATENT DOCUMENTS

| | | | |
|---|---|---|---|
| 9,593,165 | B2 | 3/2017 | Kurosawa et al. |
| 2012/0087861 | A1 | 4/2012 | Nitsch et al. |
| 2015/0140041 | A1* | 5/2015 | Vitiello .............. A61K 39/4611 424/277.1 |
| 2016/0122426 | A1 | 5/2016 | Doh et al. |
| 2019/0187132 | A1 | 6/2019 | Braasch et al. |

FOREIGN PATENT DOCUMENTS

| | | | | |
|---|---|---|---|---|
| WO | WO-2006066229 A2 * | 6/2006 | ............ | C07K 16/00 |
| WO | 2013067057 A1 | 5/2013 | | |
| WO | 2017019848 A1 | 2/2017 | | |
| WO | 2018006067 A1 | 1/2018 | | |
| WO | 2021055973 A2 | 3/2021 | | |

OTHER PUBLICATIONS

MacCallum et al., Antibody-antigen Interactions: Contact Analysis and Binding Site Topography, 1996, Journal of Molecular Biology, 262: p. 732-745. (Year: 1996).*
Rudikoff et al, Single amino acid substitution altering antigen binding specificity, 1982, 79:1979-1983 (Year: 1982).*
Casset et al, A peptide mimetic of an anti-CD4 monoclonal antibody by rational design, 2003, 307: 198-205 (Year: 2003).*
Holm et al, Functional mapping and single chain construction of the anti-cytokeratin 8 monoclonal antibody TS1, 2007: 1075-1084 (Year: 2007).*
Chen et al, Selection and Analysis of an Optimized Anti-VEGF Antibody: Crystal Structure of an Affinity-matured Fab in Complex with Antigen, J. Mol. Biol., 1999, 293, pp. 865-881 (Year: 1999).*
De Boer, Nadine L. et al., "Adjuvant dendritic cell based immunotherapy (DCBI) after cytoreductive surgery (CRS) and hyperthermic intraperitoneal chemotherapy (HIPEC) for peritoneal mesothelioma, a phase II single centre open-label clinical trial: rationale and design of the MESOPEC trial," BMJ, 2019, vol. 9, 9 pages.
Ha, Kevin D. et al., "High-content Analysis of Antibody Phage display Library Selection Outputs Identifies Tumor Selective Macropinocytosis-dependent Rapidly Internalizing Antibodies," Molecular & Cellular Proteomics, 13(12):3320-3331.
Interntaional Search Report and Written Opinion issued on Mar. 8, 2021, in International Patent Application No. PCT/US20/51853.
Krag, David N. et al., "Selection of Tumor-binding Ligands in Cancer Patients with Phage Display Libraries," 2006, Cancer Res., vol. 66, No. 15, pp. 7724-7733.
Maier, Tanja et al., "Vaccination of patients with cutaneous T-cell lumphoma using intranodal injection of autologous tumor-lysate-pulsed dendritic cells," Blood, Oct. 1, 2003, vol. 3, No. 7, pp. 2338-2344.
Belderbos, Robert A. et al: "Enhancing Dendritic Cell Therapy in Solid Tumors with Immunomodulating Conventional Treatment", Molecular Therapy—Oncolytics, vol. 13, Jun. 1, 2019 (Jun. 1, 2019), pp. 67-81, XP055968901.
Ingegnere, Tiziano et al., "Human Car NK Cells: A New Non-viral Method Allowing High Efficient Transfection and Strong Tumor Cell Killing", Frontiers in Immunology, vol. 10, Apr. 30, 2019 (Apr. 30, 2019), p. 957, XP055740362.
Jakobsen, Charlotte G et al., "Phage display derived human monoclonal antibodies isolated by binding to the surface of live primary breast cancer cells recognize GRP78", Cancer Research, vol. 67, No. 19, Oct. 1, 2007 (Oct. 1, 2007), pp. 9507-9517, XP002576192.

(Continued)

*Primary Examiner* — Mark Halvorson
*Assistant Examiner* — Dennis J Sullivan
(74) *Attorney, Agent, or Firm* — Prosyal Group, PC

(57) ABSTRACT

The present disclosure relates to a method for obtaining an antibody or antigen-binding fragment thereof that specifically binds to and against a tumor sample, comprising: administering autologous dendritic cells to a subject; taking immune cells and a tumor sample from the subject; constructing an antibody library of the immune cells; and screening the antibody library to obtain the antibody or a fragment thereof specifically binding to and against the tumor sample. The disclosure also relates to a method for engineering immune cells, an antibody or antigen-binding fragment thereof that specifically binds to and against a tumor sample and uses thereof.

10 Claims, 6 Drawing Sheets
Specification includes a Sequence Listing.

(56) References Cited

OTHER PUBLICATIONS

Li, Feng et al, "Construction and development of a mammalian cell-based full-length antibody display library for targeting hepatocellular carcinoma", Applied Microbiology and Biotechnology, vol. 96, No. 5, Jul. 7, 2012 (Jul. 7, 2012), pp. 1233-1241, XP035135332.

Lim, Wendell A et al, "The Principles of Engineering Immune Cells to Treat Cancer", Cell, vol. 168, No. 4, Feb. 9, 2017 (Fev. 9, 2017), pp. 724-740, XP029935435.

Novinger, Leah J et al, "Identification of tumor-binding scFv derived from clonally related B cells in tumor and lymph node of a patient with breast cancer", Cancer Immunology Immunotherapy, vol. 64, No. 1, Sep. 27, 2014 (Sep. 27, 2014), pp. 29-39, XP035417405.

Sabado, Rachel Lubong et al, "Directing dendritic cell immunotherapy towards successful cancer treatment", Immunotherapy, vol. 2, No. 1, Jan. 1, 2010 (Jan. 1, 2010), pp. 37-56, XP055235751.

Sun Y et al, "Phage-display selection on tumor histological specimens with laser capture microdissection", Journal of Immunological Methods, vol. 347, No. 1-2, Aug. 15, 2009 (Aug. 15, 2009), pp. 46-53, XP026337372.

Supplementary European Search Report (EESR) received in EP Patent Application No. 20866573.7 dated Oct. 18, 2022.

\* cited by examiner

PERSONALIZED CANCER IMMUNOTHERAPY

RELATED APPLICATIONS

This application claims the benefit of U.S. Provisional Patent Application No. 62/903,416, filed on Sep. 20, 2019, which is incorporated herein by reference in its entirety.

Sequence Listing

The instant application contains a Sequence Listing which has been filed electronically in ASCII format and is hereby incorporated by reference in its entirety. Said ASCII copy, created on Dec. 17, 2020, is named G4590-10100US Seq-Listing.txt and is 11 kilobytes in size.

FIELD OF THE DISCLOSURE

The present disclosure relates to a field of cancer immunotherapy. Particularly, the present disclosure relates to methods for obtaining an antibody for personalized cancer immunotherapy.

BACKGROUND OF THE DISCLOSURE

Precision medicine and immunotherapy are currently two of the hottest areas of cancer research. Immunotherapy aims to stimulate (or restore) the patient's own immune system to combat cancer. One type of personalized immunotherapy which has already been approved for patient use is chimeric antigen receptor (CAR)-T cell therapy, a novel immuno-oncology treatment modality.

There is a need for technologies that can achieve more effective personalized cancer immunotherapy against cancers.

SUMMARY OF THE DISCLOSURE

The present disclosure provides a method for obtaining an antibody or antigen-binding fragment thereof that specifically binds to and against a tumor in a subject suffering from the tumor, comprising:
  taking a tumor sample from the subject;
  administering dendritic cells to the subject to prime anti-tumor immune response;
  harvesting immune cells of the subject;
  constructing an antibody library of the immune cells; and
  screening the antibody library to obtain the antibody or a fragment thereof specifically binding to and against the tumor.

In one embodiment, the subject undergoes surgical resection or simultaneous chemotherapy and radiotherapy.

In one embodiment, the subject undergoes surgical resection or simultaneous chemotherapy and radiotherapy before the administration of the dendritic cells.

In one embodiment, the tumor sample is obtained before the administration of the dendritic cells.

In one embodiment, the dendritic cells are autologous or heterologous; preferably are autologous. In a further embodiment of the disclosure, the autologous dendritic cells are collected from the subject either before or after the subject undergoes radiation therapy, chemotherapy or surgery. In another further embodiment, the autologous dendritic cells are derived from monocytes that are collected from the subject either before or after the subject receives radiation therapy, chemotherapy or surgery.

In one embodiment of the disclosure, the dendritic cells are administered to the subject more than one time. In one embodiment, the dendritic cells are administered more than twice in a time interval. In one embodiment, the dendritic cells are administered twice. In another embodiment, the time interval is once a week. In one embodiment, the dendritic cells are administered twice a week.

In one embodiment, the method comprises:
  taking a tumor sample from the subject;
  administering dendritic cells to the subject twice a week to prime anti-tumor immune response after the subject undergoes surgical resection or simultaneous chemotherapy and radiotherapy;
  harvesting immune cells of the subject;
  constructing an antibody library of the immune cells; and
  screening the antibody library to obtain the antibody or a fragment thereof specifically binding to and against the tumor sample.

In one embodiment of the disclosure, the dendritic cells are administered to the subject with a dose of $10^4$ cells/kg body weight to $10^8$ cells/kg body weight. In a further embodiment, the dendritic cells are administered to the subject with a dose of $10^4$ cells/kg body weight to $10^6$ cells/kg body weight.

In one embodiment, the immune cells described herein are derived from peripheral blood mononuclear cells (PBMCs).

In one embodiment of the disclosure, the immune cells described herein are B cells as majority of combinatorial antibody gene library construction.

In one embodiment of the disclosure, the antibody library is constructed by phage display.

In one embodiment of the disclosure, the method further comprises establishing a primary tumor cell line from the tumor sample and screening the antibody library with the primary tumor cell line.

In one embodiment of the disclosure, the antibody library is screened by cell-based panning.

In one embodiment of the disclosure, the antibody or a fragment thereof is a monoclonal antibody, chimeric antibody, humanized antibody, human antibody or scFv antibody or a fragment thereof.

In one embodiment of the disclosure, the antibody is an anti-carbonic anhydrase IX (CAIX) antibody.

In one embodiment of the disclosure, the tumor is a squamous cell cancer, a lung cancer, a cancer of the peritoneum, a hepatocellular cancer, a gastric or stomach cancer including gastrointestinal cancer, a pancreatic cancer, a glioblastoma, a cervical cancer, an ovarian cancer, a liver cancer, a bladder cancer, a cancer of the urinary tract, a hepatoma, a breast cancer, a colon cancer, a rectal cancer, a colorectal cancer, an endometrial or uterine carcinoma, a salivary gland carcinoma, a kidney or a renal cancer, a prostate cancer, an vulval cancer, a thyroid cancer, a hepatic carcinoma, an anal carcinoma, a penile carcinoma, a melanoma, a multiple myeloma, B-cell lymphoma, a brain cancer, a head and neck cancer, or an associated metastases thereof.

The present disclosure also provides a method for engineering immune cells that specifically binds to and against a tumor sample, comprising:
  obtaining an antibody or antigen-binding fragment thereof that specifically binds to and against a tumor sample according to the method mentioned above;
  providing immune cells; and
  expressing the antibody or antigen-binding fragment thereof on the surface of the immune cells.

In one embodiment of the disclosure, the immune cells are chimeric antibody immune cells.

The present disclosure also provides an antibody or antigen-binding fragment thereof that specifically binds to and against a tumor sample, which comprises complementarity determining regions (CDRs) of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and wherein:

the CDRH1 region comprises the amino acid sequence of SEQ ID NO: 1 (SYAMQ); the CDRH2 region comprises the amino acid sequence selected from the group consisting of SEQ ID NOs: 2 (GMSDDGSWTDYGAAVKG) and 3 (GVSDDGSWTGYGAAVQG);

the CDRH3 region comprises the amino acid sequence selected from the group consisting of SEQ ID NOs: 4 (GAGTGYCDNRSFGCASTIDA) and 5 (GAGTGYCNNRGFGCASTIDA); and the CDRL1 region comprises the amino acid sequence of SEQ ID NO: 6 (SGSSGSYG);

the CDRL2 region comprises the amino acid sequence selected from the group consisting of SEQ ID NOs: 7 (HNDKRPS) and 8 (YNDKRPS); the CDRL3 region comprises the amino acid sequence of SEQ ID NO: 9 (GSADRSGAGI).

In one embodiment of the disclosure, the antibody or antigen-binding fragment thereof is a mammalian antibody.

In one embodiment of the disclosure,
the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 4; and the CDRL1 region comprises the amino acid sequence of SEQ ID NO: 6; the CDRL2 region comprises the amino acid sequence of SEQ ID NO: 7; the CDRL3 region comprises the amino acid sequence of SEQ ID NO: 9.

In one embodiment of the disclosure,
the CDRH1 region comprises the amino acid sequence of SEQ ID NO: 1; the CDRH2 region comprises the amino acid sequence of SEQ ID NO: 3; the CDRH3 region comprises the amino acid sequence of SEQ ID NO: 5; and the CDRL1 region comprises the amino acid sequence of SEQ ID NO: 6; the CDRL2 region comprises the amino acid sequence of SEQ ID NO: 8; the CDRL3 region comprises the amino acid sequence of SEQ ID NO: 9.

In one embodiment of the disclosure, the antibody or antigen-binding fragment thereof comprises a heavy chain variable region comprising the amino acid sequence of SEQ ID NO: 10 (AVTLDESGGGLHTPGG-GLSLVCRASGFTFSSYAMQWVRQAPGK-GLEWVAGMSDDGS WTDYGAAVKGRATIS-RDNGQSTVRLQLNNLRAEDTGTYYCAKGAGTGYC-DNRSFGCA STIDAWGHGTEVIVSS); and a light chain variable region comprising the amino acid sequence of SEQ ID NO: 11 (AL-TQPSSVSANLGETVEITCSGSSGSYGWYQQK-SPGSAPVTVIYHNDKRPSDIPSRFSGS KSG-STGTLTITGVQAEDEAVYYCGSADRSGAGIFGAGTTL TVL).

In one embodiment of the disclosure, the antibody or antigen-binding fragment thereof which comprises a heavy chain variable region comprising the amino acid sequence of SEQ ID NO: 12 (AVTLDESGGGLQTPGG-GLSLVCRASGFTMTSYAMQWVRQAPGK-GLEWVAGVSDDGS WTGYGAAVQGRATIS-RDNGQSTVRLLLNNLRAEDTATYYCVKGAGTGYCN NRGFGCA STIDAWGHGTEVIVSS); and a light chain variable region comprising the amino acid sequence of SEQ ID NO: 13 (AL-TQPSSVSANLGETVEITCSGSSGSYGWYQQK-SPGSAPVTVIYYNDKRPSDIPSRFSGS KSG-STGTLTITGVQAEDEAVYYCGSADRSGAGIFGAGTT LTVL).

In one embodiment of the disclosure, the antibody or antigen-binding fragment thereof which comprises the amino acid sequence selected from the group consisting of SEQ ID NOs: 14 (AL-TQPSSVSANLGETVEITCSGSSGSYGWYQQK-SPGSAPVTVIYHNDKRPSDIPSRFSGS KSG-STGTLTITGVQAEDEAVYYCGSADRSGAGIFGAGTT-LTVLGQSSRSSGGGGSSGGG GSAVTLDESGG-GLHTPGGGLSLVCRASGFTFSSYAMQWVRQAPGK-GLEWVAGMSDDG SWTDYGAAVKGRATIS-RDNGQSTVRLQLNNLRAEDTGTYYCAKGAGTGYC-DNRSFGC ASTIDAWGHGTEVIVSS) and 15 (AL-TQPSSVSANLGETVEITCSGSSGSYGWYQQK-SPGSAPVTVIYYNDKRPSDIPSRFSGS KSG-STGTLTITGVQAEDEAVYYCGSADRSGAGIFGAGTT-LTVLGQSSRSSAVTLDESGG GLQTPGG-GLSLVCRASGFTMTSYAMQWVRQAPGK-GLEWVAGVSDDGSWTGYGAAVQ GRATIS-RDNGQSTVRLLLNNLRAEDTATYYCVKGAGTGYC-NNRGFGCASTIDAWGHGT EVIVSS).

In one embodiment of the disclosure, the antibody or antigen-binding fragment thereof is expressed on a surface of an immune cell.

The present disclosure provides a pharmaceutical composition comprising a therapeutically effective amount of the antibody or antigen-binding fragment thereof mentioned above and optionally a pharmaceutically acceptable carrier or excipient.

The present disclosure provides use of the pharmaceutical composition mentioned above in the manufacture of a medicament for treating tumor in a subject in need.

In one embodiment of the disclosure, the medicament is administered intravenously, intra-peritoneally, intra-arterially, intra-thecally, intra-vesically, or intratumorally.

The present disclosure provides a method for treating tumor in a subject in need comprising administering the pharmaceutical composition mentioned above.

In one embodiment of the disclosure, wherein the administering is intravenously, intra-peritoneally, intra-arterially, intra-thecally, intra-vesically, or intratumorally.

DETAILED DESCRIPTION OF THE DISCLOSURE

Figure 1:
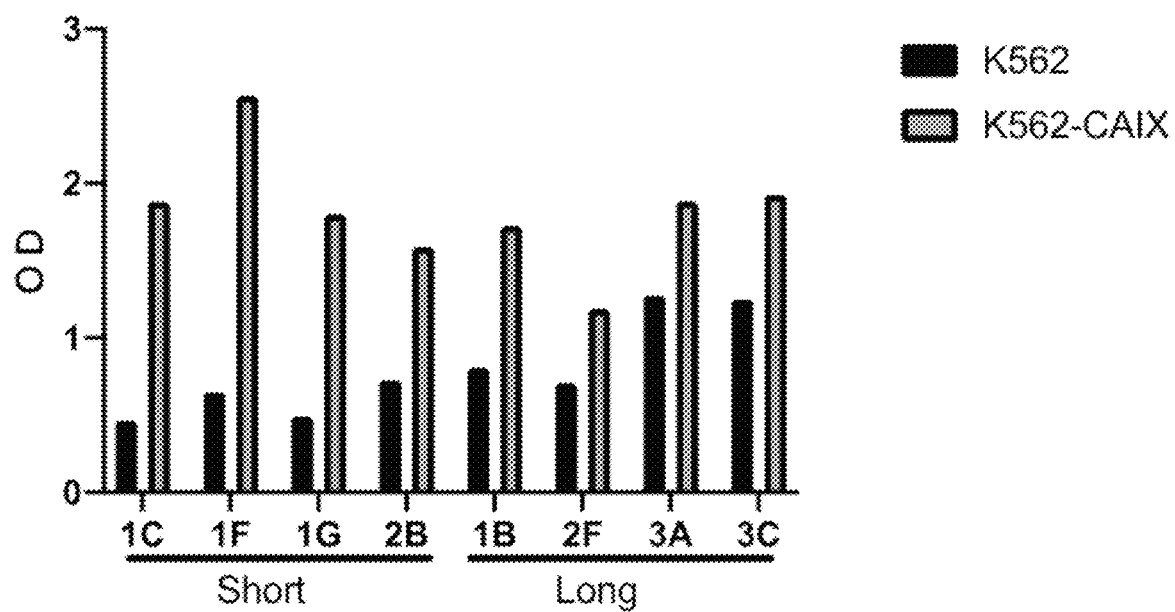
FIG. 1 shows the results of exemplary cell-based ELISA of K562-CAIX.

To facilitate an understanding of the present technology, a number of terms and phrases are defined below. Additional definitions are set forth throughout the detailed description.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "specifically binds" means that an antibody does not cross react to a significant extent with other epitopes.

As used herein, the term "epitope" refers to the site on the antigen to which an antibody binds to.

As used herein, the term "antibody" refers to single chain, two-chain, and multi-chain proteins and polypeptides belonging to the classes of polyclonal, monoclonal, chimeric, and humanized antibodies; it also includes synthetic and genetically engineered variants of these antibodies. "Antibody fragment" includes Fab, Fab', F(ab')2, and FIT fragments, as well as any portion of an antibody having specificity toward a desired target epitope or epitopes.

As used herein, the term "monoclonal antibody" refers to an antibody obtained from a population of substantially homogeneous antibodies. In other words, a monoclonal antibody consists of a homogeneous antibody arising from the growth of a single cell clone (for example a hybridoma, a eukaryotic host cell transfected with a DNA molecule coding for the homogeneous antibody or a prokaryotic host cell transfected with a DNA molecule coding for the homogeneous antibody). These antibodies are directed against a single epitope and are therefore highly specific.

As used herein, the term "humanized antibody" refers to a recombinant protein in which the CDRs from an antibody from one species; e.g., a murine or a chicken antibody, are transferred from the heavy and light variable chains of the antibody from the species into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody. The humanized antibody may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present disclosure include that disclosed in Padlan, Mol. Immunol., 31(3):169-217 (1994).

As used herein, the term "chimeric antibody" refers to a recombinant protein that contains the variable domains of both the heavy and light antibody chains, including the complementarity determining regions (CDRs) of an antibody derived from one species, preferably a rodent antibody or a chicken antibody, more preferably a murine antibody, while the constant domains of the antibody molecule are derived from those of a human antibody.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

As used herein, the term "sample" encompasses a variety of sample types obtained from an individual, subject or patient and can be used in a diagnostic or monitoring assay. The definition encompasses blood and other liquid samples of biological origin, solid tissue samples such as a biopsy specimen or tissue cultures or cells derived therefrom and the progeny thereof.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of an antibody that, when administered to a mammal or other subject for treating a disease, is sufficient to effect such treatment for the disease.

The present disclosure provides a method for obtaining an antibody or antigen-binding fragment thereof that specifically binds to and against a tumor in a subject suffering from tumor, comprising:

taking a tumor sample from the subject;
administering dendritic cells to the subject to prime anti-tumor immune response;
harvesting immune cells of the subject;
constructing an antibody library of the immune cells; and
screening the antibody library to obtain the antibody or a fragment thereof specifically binding to and against the tumor.

In one embodiment, a tumor sample is taken to establish a specific primary tumor cell line. In one embodiment, the immune cells described herein are derived from peripheral blood mononuclear cells (PBMCs).

It is believed, though not intended to be restricted by any theoretical, that dendritic cells are antigen-presenting cells of the mammalian immune system, which present antigens on the cell surface to the T cells of the immune system. Administering autologous dendritic cells before harvesting immune cells improves the specificity and effectivity of screening, facilitating obtaining the powerful antibody that specifically binds to and against a tumor sample. The autologous dendritic cells may be derived from the monocytes of the subject or provided through proliferation. Preferably, the dendritic cells are derived from the PBMCs of the subject; more preferably directly from the peripheral blood.

In preferred embodiments, the subject is a mammal. Exemplary mammals include human, pig, sheep, goat, horse, mouse, dog, cat, cow, etc.

Clinically, tumor patients often undergo radiation therapy, chemotherapy or surgery. In order to collect effective dendritic cells, the dendritic cells are preferably collected from the subject before the subject undergoes radiation therapy, chemotherapy or surgery. The duration between the radiation therapy, chemotherapy or surgery and collection may be 1, 2, 3, 4, 5, 6, 7, 8, 9, 10, 11, 12, 13, or 14 days, preferably, 7 days.

The administration of the dendritic cells may be performed more than one time; preferably, the dendritic cells are administered to the subject twice in a time interval. The interval between the administrations may be 1, 2, 3, 4, 5, 6, 7, 8, 9, 10, 11, 12, 13, or 14 days, preferably, 7 days.

In another aspect, the dendritic cells are administered to the subject in an amount sufficient to exhibit antigen presentation. Preferably, the dendritic cells are administered to the subject with a dose of $10^4$ cells/kg body weight to $10^6$ cells/kg body weight.

In situation of the subject receiving radiation therapy, chemotherapy or surgery, the dendritic cells are preferably administered to the subject after the subject undergoes radiation therapy, chemotherapy or surgery.

The immune cells harvested may be from the lymph or blood, preferably from the peripheral blood. Preferably, the immune cells are harvested after 1, 2, 3, 4, 5, 6, 7, 8, 9, 10, 11, 12, 13, or 14 days, preferably 7 days, of the administration of dendritic cells.

Examples of the immune cells according to the disclosure include but are not limited to lymphocytes, neutrophils, monocytes and macrophages. Preferably, the immune cells are lymphocytes. Examples of the lymphocytes include but are not limited to T-cells, B-cells and NK cells. Preferably, the immune cells are B cells.

The manner for constructing an antibody library of the immune cells may be varied. Examples of the construction include but are not limited to phage display, in vitro display, yeast display, mammalian display, and bacterial display; preferably, the antibody library is constructed by phage display.

The tumor sample may be provided directly from the subject or processed. Preferably, the method further comprises establishing a primary tumor cell line from the tumor sample and screening the antibody library with the primary tumor cell line. Moreover, the antibody library is preferably screened by cell-based panning.

The antibody or a fragment thereof may be a monoclonal antibody, chimeric antibody, humanized antibody, human antibody or scFv antibody or a fragment thereof; preferably scFv antibody.

In one embodiment of the disclosure, an anti-carbonic anhydrase IX (CAIX) antibody is screened according to the disclosure.

Tumors that may be treated with the antibody or a pharmaceutical composition thereof include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The present disclosure also provides a method for engineering immune cells that specifically binds to and against a tumor sample, comprising:

obtaining an antibody or antigen-binding fragment thereof that specifically binds to and against a tumor sample according to the method mentioned above;
providing immune cells; and
expressing the antibody or antigen-binding fragment thereof to the immune cells.

Preferably, the immune cells are chimeric antibody immune cells. In one embodiment of the disclosure, the chimeric antibody comprises an antigen recognition domain, hinge region, transmembrane domain, and intracellular T-cell signaling domain. The antibody or antigen-binding fragment thereof is as the antigen recognition domain The present disclosure also provides an antibody or antigen-binding fragment thereof that specifically binds to and against a tumor sample, which comprises complementarity determining regions (CDRs) of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and wherein:

the CDRH1 region comprises the amino acid sequence of SEQ ID NO: 1 (SYAMQ); the CDRH2 region comprises the amino acid sequence selected from the group consisting of SEQ ID NOs: 2 (GMSDDGSWTDYGAAVKG) and 3 (GVSDDGSWTGYGAAVQG);

the CDRH3 region comprises the amino acid sequence selected from the group consisting of SEQ ID NOs: 4 (GAGTGYCDNRSFGCASTIDA) and 5 (GAGTGYCNNRGFGCASTIDA); and the CDRL1 region comprises the amino acid sequence of SEQ ID NO: 6 (SGSSGSYG);

the CDRL2 region comprises the amino acid sequence selected from the group consisting of SEQ ID NOs: 7 (HNDKRPS) and 8 (YNDKRPS); the CDRL3 region comprises the amino acid sequence of SEQ ID NO: 9 (GSADRSGAGI).

Particularly, the antibody or antigen-binding fragment thereof is anti-CAIX L3A, wherein:

the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 4; and the CDRL1 region comprises the amino acid sequence of SEQ ID NO: 6; the CDRL2 region comprises the amino acid sequence of SEQ ID NO: 7; the CDRL3 region comprises the amino acid sequence of SEQ ID NO: 9.

Particularly, the antibody or antigen-binding fragment thereof is anti-CAIX S1C, wherein:

the CDRH1 region comprises the amino acid sequence of SEQ ID NO: 1; the CDRH2 region comprises the amino acid sequence of SEQ ID NO: 3; the CDRH3 region comprises the amino acid sequence of SEQ ID NO: 5; and the CDRL1 region comprises the amino acid sequence of SEQ ID NO: 6; the CDRL2 region comprises the amino acid sequence of SEQ ID NO: 8; the CDRL3 region comprises the amino acid sequence of SEQ ID NO: 9.

Preferably, anti-CAIX L3A comprises a heavy chain variable region comprising the amino acid sequence of SEQ ID NO: 10 (AVTLDESGGGLHTPGGGLSLVCRASGFTFSSYAMQWVRQAPGKGLEWVAGMSDDGS WTDYGAAVKGRATISRDNGQSTVRLQLNNLRAEDTGTYYCAKGAGTGYCDNRSFGCA STIDAWGHGTEVIVSS); and a light chain variable region comprising the amino acid sequence of SEQ ID NO: 11 (AL-TQPSSVSANLGETVEITCSGSSGSYGWYQQK-SPGSAPVTVIYHNDKRPSDIPSRFSGS KSG-STGTLTITGVQAEDEAVYYCGSADRSGAGIFGAGTTL TVL).

Preferably, anti-CAIX S1C comprises a heavy chain variable region comprising the amino acid sequence of SEQ ID NO: 12 (AVTLDESGGGLQTPGGGLSLVCRASGFTMTSYAMQWVRQAPGKGLEWVAGVSDDGS WTGYGAAVQGRATISRDNGQSTVRLLLNNLRAEDTATYYCVKGAGTGYCNNRGFGCA STIDAWGHGTEVIVSS); and a light chain variable region comprising the amino acid sequence of SEQ ID NO: 13 (AL-TQPSSVSANLGETVEITCSGSSGSYGWYQQK-SPGSAPVTVIYYNDKRPSDIPSRFSGS KSG-STGTLTITGVQAEDEAVYYCGSADRSGAGIFGAGTTL TVL).

More preferably, anti-CAIX L3A comprises the amino acid sequence of SEQ ID NO: (AL-TQPSSVSANLGETVEITCSGSSGSYGWYQQK-SPGSAPVTVIYHNDKRPSDIPSRFSGS KSG-STGTLTITGVQAEDEAVYYCGSADRSGAGIFGAGTTL TVLGQSSRSSGGGGSSGGG GSAVTLDESGG-GLHTPGGGLSLVCRASGFTFSSYAMQWVRQAPGK-GLEWVAGMSDDG SWTDYGAAVKGRATIS-RDNGQSTVRLQLNNLRAEDTGTYYCAKGAGTGYCD NRSFGC ASTIDAWGHGTEVIVSS).

More preferably, anti-CAIX S1C comprises the amino acid sequence of SEQ ID NO: (AL-TQPSSVSANLGETVEITCSGSSGSYGWYQQK-SPGSAPVTVIYYNDKRPSDIPSRFSGS KSG-STGTLTITGVQAEDEAVYYCGSADRSGAGIFGAGTTL TVLGQSSRSSAVTLDESGG GLQTPGG-GLSLVCRASGFTMTSYAMQWVRQAPGK-GLEWVAGVSDDGSWTGYGAAVQ GRATIS-RDNGQSTVRLLLNNLRAEDTATYYCVKGAGTGYCN NRGFGCASTIDAWGHGT EVIVSS).

In one preferred embodiment of the disclosure, the antibody or antigen-binding fragment thereof is conjugated with a therapeutic agent. In one preferred embodiment of the disclosure, the antibody or antigen-binding fragment thereof is expressed on the surface of a cell. More preferably, the cell is an immune cell, still more preferably, NK-cell.

The present disclosure provides a pharmaceutical composition comprising a therapeutically effective amount of the antibody or antigen-binding fragment thereof mentioned above and optionally a pharmaceutically acceptable carrier or excipient. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbo-wax (polyethylene glycols of various molecular weights), semi-solid gels, and semi-solid mixtures containing carbo-wax.

The dose of antibody administered to a patient may vary depending upon the age and the size of the patient, target disease, conditions, route of administration, and the like. The preferred dose is typically calculated according to body weight or body surface area. When an antibody of the present disclosure is used for treating tumor in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, intra-arterial, intra-thecal, intra-vesical, or intra-tumoral, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Preferably, the medicament is administered intravenously, intra-peritoneally, intra-arterially, intra-thecally, intra-vesically, or intratumorally.

The present disclosure provides use of the pharmaceutical composition mentioned above in the manufacture of a medicament for treating tumor in a subject in need.

The present disclosure provides a method for treating tumor in a subject in need comprising administering the pharmaceutical composition mentioned above.

In one embodiment of the disclosure, wherein the administering is intravenously, intra-peritoneally, intra-arterially, intra-thecally, intra-vesically, or intratumorally.

The following examples are provided to aid those skilled in the art in practicing the present disclosure.

EXAMPLES

Example 1: Expression, Purification Binding Assay of Anti-CAIX Ab

K562 cells were taken for negative selection; meanwhile, CAIX-overexpression K562 cells were taken for positive selection. Antibody phage library was established from chickens immunized with CAIX Ag.

The antibody libraries were established based on the previous report (Andris-Widhopf J, Rader C, Steinberger P et al. Methods for the generation of chicken monoclonal antibody fragments by phage display. *J Immunol Methods* 2000; 242: 159-81). Briefly, spleens harvested from chickens following the final immunization were placed immediately in Trizol (Gibco BRL., USA) for homogenization. Ten μg of total RNA was reversely transcribed into the first-strand cDNA using a SuperScript RT kit (Invitrogen, USA). After amplification using chicken-specific primers, PCR products of heavy and light chain variable (VH and VL) regions were subjected to a second round of PCR to form full-length scFv fragments with a short or long linker, which were further digested with SfiI and cloned into the pComb3X vector. Recombinant phage DNAs were transformed into *E. coli* ER2738 strain by electroporation (MicroPulser from Bio-Rad). The production of recombinant phages was initiated by the addition of wild-type VCS-M13 helper phage, which were subsequently precipitated with 4% polyethylene glycol 8000 and 3% NaCl (w/v), and finally re-suspended in 1× phosphate-buffered saline (PBS) containing 1% bovine serum albumin (BSA). Then, $10^{12}$~$10^{13}$ plaque-forming units (pfu) of recombinant phages (50 ul) in the scFv antibody libraries were blocked with 1% BSA in PBS at 4° C. for 1 hr and then incubated with $10^6$ K562 cell (100 ul) at RT for 30 mins for twice (Negative selection). After the unbound phages supernatant were collected, the supernatant were incubated with CAIX-overexpression K562 cells at 4° C. for 1 hr (positive selection). Then the cells were wash with PBS for 5~8 times. Bound phages were eluted with 0.2M glycine-HCl (pH 2.2), neutralized with 1 M Tris-HCl buffer and then used to infect the *E. coli* ER2738 strain. The amplified phages were precipitated and recovered as described above for the next round of selection.

The libraries with short linker and long linker were constructed as shown in Table 1. The elution titer after each panning are shown (Table 1). After three rounds of panning, the CAIX binding phage variants were greatly enriched. These results suggested the non-specific binding phage was removed throughout the panning process and the clones with specific binding affinity were enriched. The sequences were confirmed to belong to chicken immunoglobulin germline gene.

TABLE 1

| Long chain linker Library | | | |
|---|---|---|---|
| | Round 1 | Round 2 | Round 3 |
| Elution | $2*10^4$ | $1*10^6$ | $4*10^6$ |
| Amplification | $2.2*10^{13}$ | $2.8*10^{13}$ | |
| Short chain linker Library | | | |
| | Round 1 | Round 2 | Round 3 |
| Elution | $7*10^4$ | $1*10^6$ | $5*10^6$ |
| Amplification | $2*10^{13}$ | $3.8*10^{12}$ | |

To examine their binding reactivity, 50 μl of candidate phage were incubated with K562 or CAIX-overexpression K562 cells in the ELISA plate wells with shaking at 150 rpm at RT for 2 hours. After washed with PBS for 3 times, the bound scFv were detected by incubating with HRP-conjugated anti-M13 antibodies (1:5,000) at RT for 2 hours. After washed with PBS for 6 times, a tetramethylbenzidine (TMB) substrate solution (Sigma, USA) was added to the wells for color development. The reaction was stopped with 2 N $H_2S)_4$ and optical density was measured at 450-540 nm using an ELISA plate reader (BioTek Synergy HT). The results of cell-based ELISA are shown in FIG. 1. The candidate scFvs have higher binding activity to CAIX-overexpression K562 cells when compared to K562 cells.

Figure 2A:
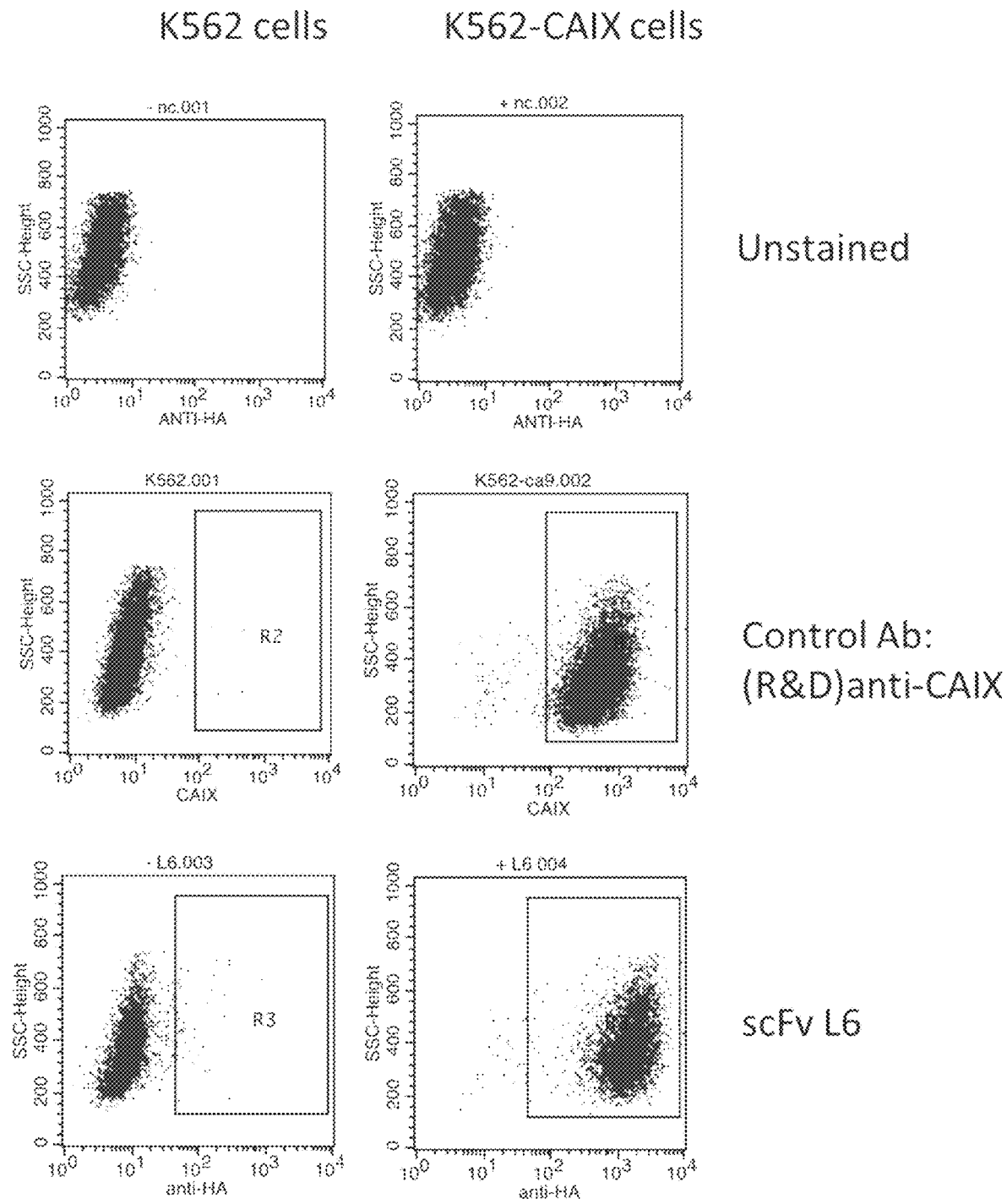
FIGS. 2A to 2C show the results of exemplary cell surface staining. 2A: unstained, control antibody (anti-CAIX); scFv L6. 2B: Long 1B, 3A, 2F, 3C antibodies. 2C: Short 1C, 1F, 1G, 2B antibodies.
Figure 2B:
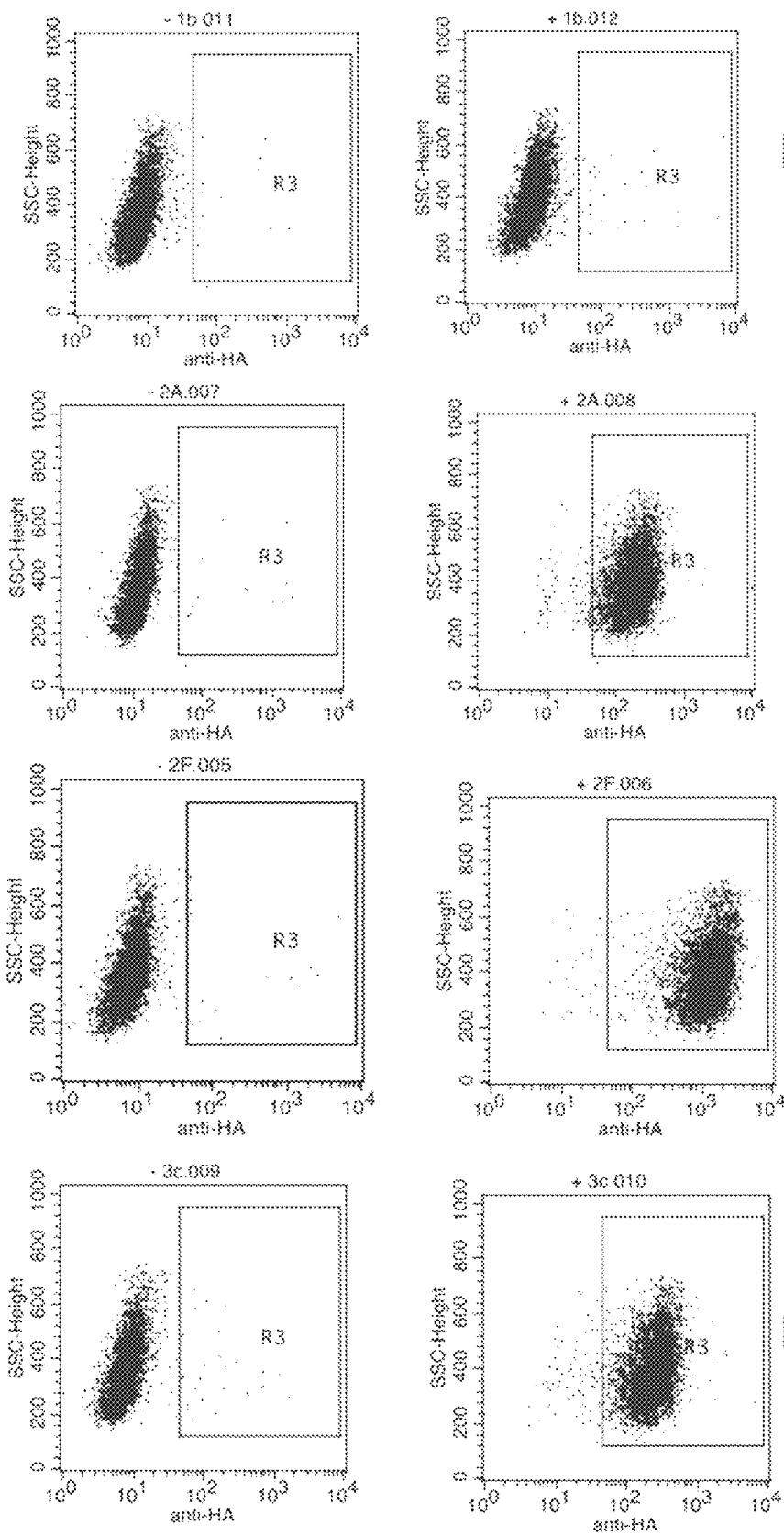
Figure 2C:
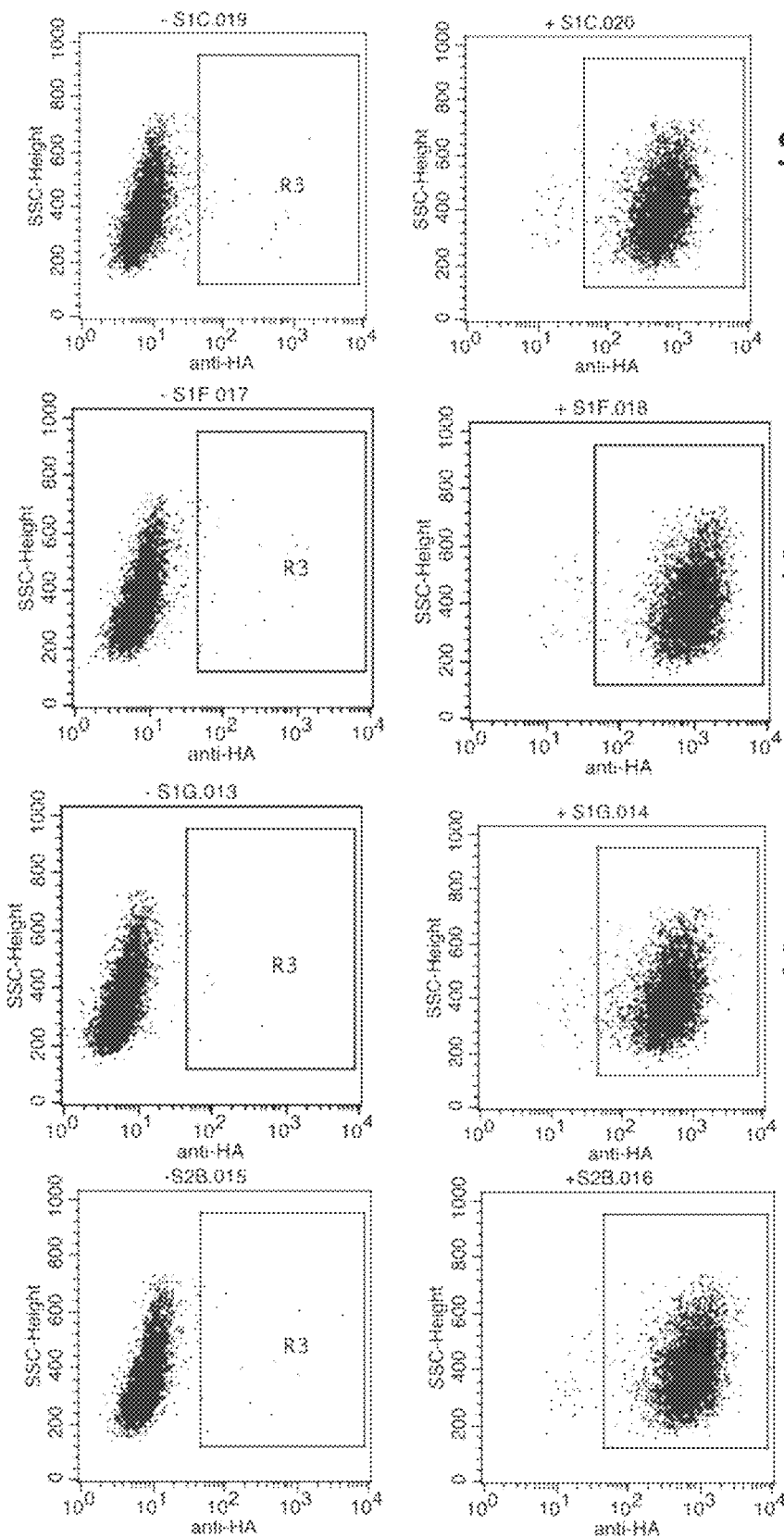

Anti-HA antibody was used to detect the binding activity of candidate phage clones. $1\times10^5$ K562 or K562-CAIX cells and 20 μl candidate phage clone were subjected to flow cytometry assay. The results of cell surface staining are shown in FIGS. 2A to 2C. Except for anti-CAIX L1B scFv, all the scFvs could specifically bind to CAIX-overexpression cells.

Among the antibodies, anti-CAIX L3A (Long 3A) and S1C (Short 1C) were obtained.

Example 2: Anti-Thyroid Cancer Cell Ab in In Vivo Assay

Figure 3:
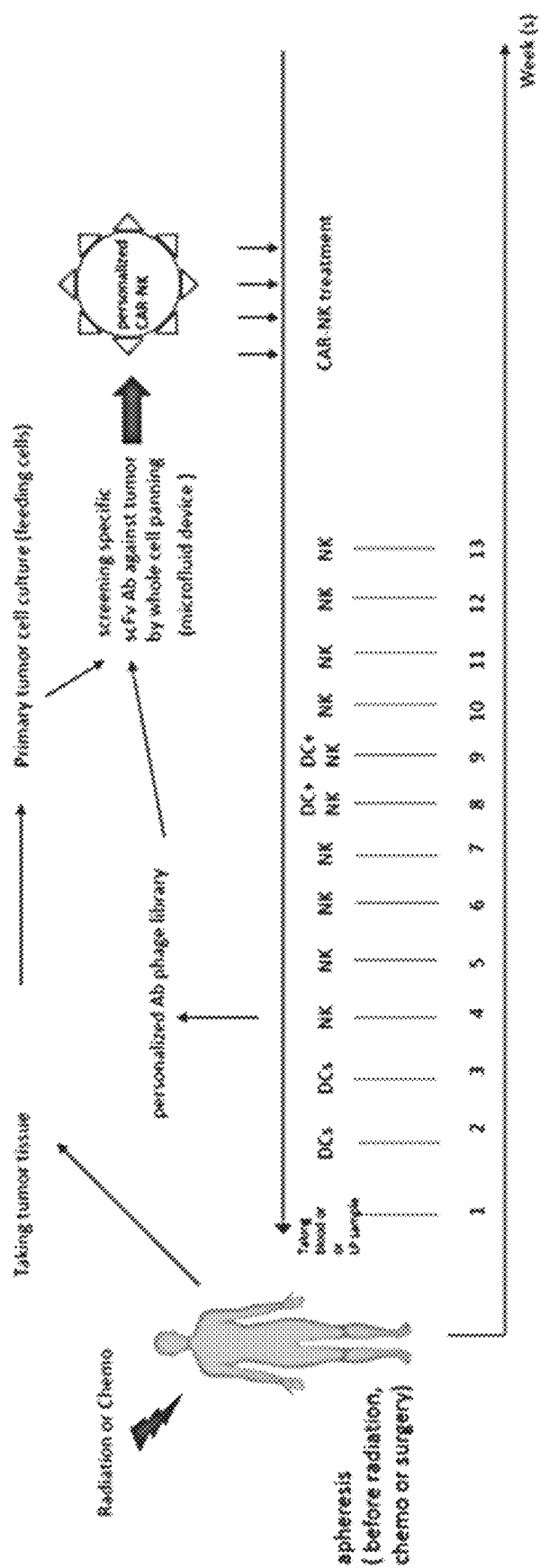
FIG. 3 shows the schematic diagram of the exemplary method for obtaining an antibody or antigen-binding fragment thereof that specifically binds to and against a tumor sample.

The schematic diagram of the method for obtaining an antibody or antigen-binding fragment thereof that specifically binds to and against a tumor sample is shown in FIG. 3.

Dendritic cells were collected from a patient suffered from thyroid cancer. After the patient underwent surgical resection or simultaneous chemotherapy and radiotherapy, the patient received axillary lymph node (ALN) injection of $1\times10^4$~$1\times10^6$ cells/kg body weight of autologous DC cells twice (at week 1 and 2). Surgical resection sample was used to establish tumor cell line, and the peripheral blood collected in the 3rd week was used to establish the Ab phage library.

Thyroid cancer cells (KYL's cells) were established from the patient and cultured in RPMI1640 medium (Hyclone, SH30027) supplemented with 1.5% PLUS' Human Plate Lysate (CPMPASS, CPS-PLS5-BAG) and 2% Penicillin-streptomycin (Life technologies, 15140) at 37° C. in humidified air with 5% $CO_2$.

The protocol of cell-based panning is as mentioned in Example 1.

The phage titer was performed according to Example 1, and the results are shown in Table 2.

TABLE 2

| | Panning 1 | Amplify 1 | Panning 2 | Amplify 2 | Panning 3 |
|---|---|---|---|---|---|
| Long Chain Linker | $1.3*10^2$ | $4*10^{11}$ | $1.5*10^5$ | $7.0*10^{11}$ | $3.7*10^5$ |
| Short Chain Linker | $1.2*10^2$ | $2*10^{10}$ | $1.1*10^5$ | $1.0*10^{12}$ | $1.22*10^6$ |

Figure 4:
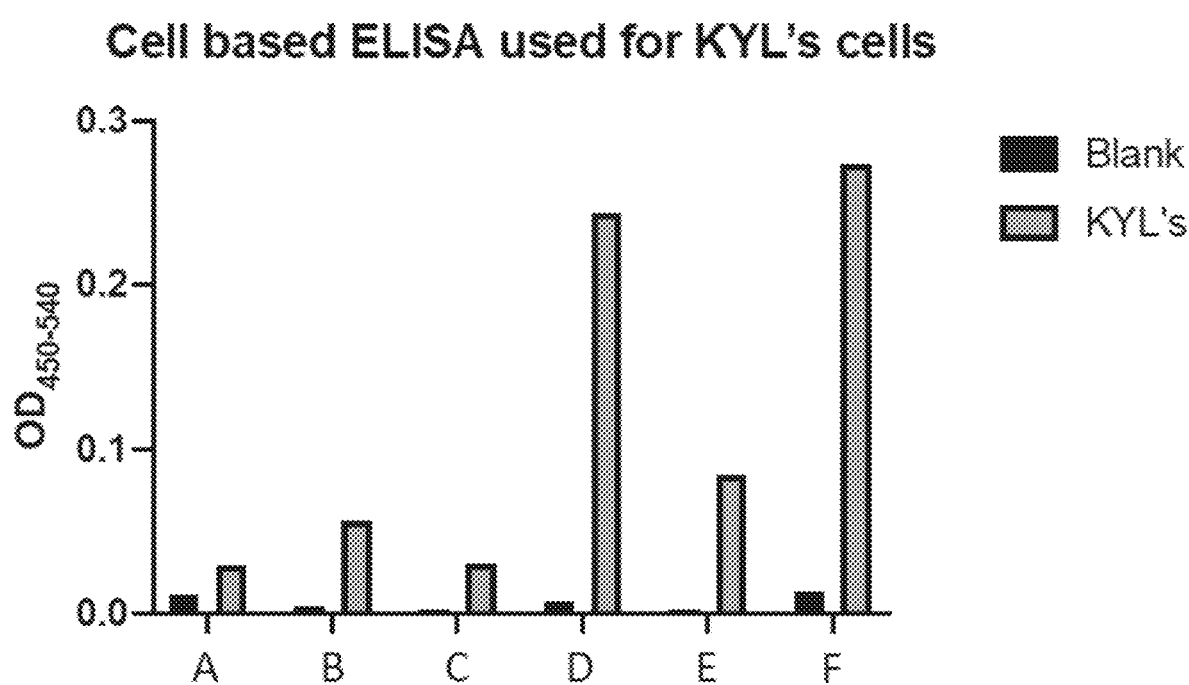
FIG. 4 shows the results of exemplary cell-based ELISA of KYL's cell.

The protocols of phage amplification and cell-based ELISA were the same to those in Example 1. The results are shown in FIG. 4. Clone D and F have high binding activity to thyroid cancer cells.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. An antibody or antigen-binding fragment thereof, comprising
a heavy chain complementarity determining regions 1 (CDRH1), a heavy chain complementarity determining regions 2 (CDRH2), a heavy chain complementarity determining regions 3 (CDRH3), a light chain complementarity determining regions 1 (CDRL1), a light chain complementarity determining regions 2 (CDRL2), and a light chain complementarity determining regions 3 (CDRL3), wherein
the CDRH1 consists of the amino acid sequence of SEQ ID NO: 1; the CDRH2 consists of the amino acid sequence of SEQ ID NO: 2 (GMSDDGSWTDYGAAVKG); the CDRH3 consists of the amino acid sequence of SEQ ID NO: 4 (GAGTGYCDNRSFGCASTIDA); and
the CDRL1 consists of the amino acid sequence of SEQ ID NO: 6; the CDRL2 consists of the amino acid sequence of SEQ ID NO: 7 (HNDKRPS); the CDRL3 consists of the amino acid sequence of SEQ ID NO: 9.

2. An engineering immune cell, comprising: an antigen recognition domain, a hinge region, a transmembrane domain, and an intracellular T-cell signaling domain, wherein the antigen recognition domain of the engineered immune cell comprises the antibody or antigen-binding fragment thereof of claim 1.

3. The antibody or antigen-binding fragment thereof, comprising
a heavy chain variable region comprising the amino acid sequence of SEQ ID NO: 10 (AVTLDESGG-GLHTPGG-GLSLVCRASGFTFSSYAMQWVRQAPGK-GLEWVAGMSDDGSWTDYGAAVKGRATISRDNG QSTVRLQLNNLRAEDTGTYYCAK-GAGTGYCDNRSFGCASTIDAWGHGTEVIVSS);
and a light chain variable region comprising the amino acid sequence of SEQ ID NO: 11 (AL-TQPSSVSANLGETVEITCSGSSGSYGWYQQK-SPGSAPVTVIYHNDKRPSDIPSRFSGSKSG-STGTLTITGVQAEDEAVYYCGSADRSGAGIFGA-GTTLTVL).

4. The antibody or antigen-binding fragment thereof of claim 1, wherein the antibody or antigen-binding fragment thereof comprises the amino acid sequence of SEQ ID NO: 14 (ALTQPSSVSANLGETVEITCSGSSGSYGWYQQK-SPGSAPVTVIYHNDKRPSDIPSRFSGSKSG-STGTLTITGVQAEDEAVYYCGSADRSGAGIFGAGT-TLTVLGQSSRSSGGGGSSGGGGSAVTLDESGGGLHT- PGGGLSLVCRASGFTFSSYAMQWVRQAPGK-
GLEWVAGMSDDGSWTDYGAAVKGRATIS-
RDNGQSTVRLQLNNLRAEDTGTYYCAK-
GAGTGYCDN SFGCASTIDAWGHGTEVIVSS).

5. The antibody or antigen-binding fragment thereof of claim 1, wherein the antibody or a fragment thereof is a monoclonal antibody, chimeric antibody, humanized antibody, human antibody or scFv antibody or a fragment thereof.

6. The antibody or antigen-binding fragment thereof of claim 1, which is expressed on a surface of an immune cell.

7. The antibody or antigen-binding fragment thereof of claim 2, wherein the antibody or antigen-binding fragment thereof is configured to be administered intravenously, intra-peritoneally, intra-arterially, intra-thecally, intra-vesically, or intratumorally.

8. The engineered immune cell of claim 2, wherein the antigen is expressed by a tumor, and the tumor is a squamous cell cancer, a lung cancer, a cancer of the peritoneum, a hepatocellular cancer, a gastric or stomach cancer including gastrointestinal cancer, a pancreatic cancer, a glioblastoma, a cervical cancer, an ovarian cancer, a liver cancer, a bladder cancer, a cancer of the urinary tract, a hepatoma, a breast cancer, a colon cancer, a rectal cancer, a colorectal cancer, an endometrial or uterine carcinoma, a salivary gland carcinoma, a kidney or a renal cancer, a prostate cancer, an vulval cancer, a thyroid cancer, a hepatic carcinoma, an anal carcinoma, a penile carcinoma, a melanoma, a multiple myeloma, B-cell lymphoma, a brain cancer, a head and neck cancer, or an associated metastases thereof.

9. An engineered immune cell, comprising an antigen recognition domain, a hinge region, a transmembrane domain, and an intracellular T-cell signaling domain, wherein the antigen recognition domain of the engineered immune cell comprises the antibody or antigen-binding fragment thereof of claim 3.

10. The antibody or antigen-binding fragment thereof of claim 3, wherein the antibody or antigen-binding fragment thereof comprises the amino acid sequence of SEQ ID NO: 14 (ALTQPSSVSANLGETVEITCSGSSGSYGWYQQK-
SPGSAPVTVIYHNDKRPSDIPSRFSGSKSG-
STGTLTITGVQAEDEAVYYCGSADRSGAGIFGAGT-
TLTVLGQSSRSSGGGGSSGGGGSAVTLDESGGGLHT-
PGGGLSLVCRASGFTFSSYAMQWVRQAPGK-
GLEWVAGMSDDGSWTDYGAAVKGRATIS-
RDNGQSTVRLQLNNLRAEDTGTYYCAK-
GAGTGYCDN SFGCASTIDAWGHGTEVIVSS).

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Homo sapiens

<400> SEQUENCE: 1

Ser Tyr Ala Met Gln
1               5

<210> SEQ ID NO 2
<211> LENGTH: 17
<212> TYPE: PRT
<213> ORGANISM: Homo sapiens

<400> SEQUENCE: 2

Gly Met Ser Asp Asp Gly Ser Trp Thr Asp Tyr Gly Ala Ala Val Lys
1               5                   10                  15

Gly

<210> SEQ ID NO 3
<211> LENGTH: 17
<212> TYPE: PRT
<213> ORGANISM: Homo sapiens

<400> SEQUENCE: 3

Gly Val Ser Asp Asp Gly Ser Trp Thr Gly Tyr Gly Ala Ala Val Gln
1               5                   10                  15

Gly

<210> SEQ ID NO 4
<211> LENGTH: 20
<212> TYPE: PRT
<213> ORGANISM: Homo sapiens

<400> SEQUENCE: 4

Gly Ala Gly Thr Gly Tyr Cys Asp Asn Arg Ser Phe Gly Cys Ala Ser
1               5                   10                  15

Thr Ile Asp Ala
            20

<210> SEQ ID NO 5
<211> LENGTH: 20
<212> TYPE: PRT
<213> ORGANISM: Homo sapiens

<400> SEQUENCE: 5

```
Gly Ala Gly Thr Gly Tyr Cys Asn Asn Arg Gly Phe Gly Cys Ala Ser
1               5                   10                  15

Thr Ile Asp Ala
            20
```

<210> SEQ ID NO 6
<211> LENGTH: 8
<212> TYPE: PRT
<213> ORGANISM: Homo sapiens

<400> SEQUENCE: 6

```
Ser Gly Ser Ser Gly Ser Tyr Gly
1               5
```

<210> SEQ ID NO 7
<211> LENGTH: 7
<212> TYPE: PRT
<213> ORGANISM: Homo sapiens

<400> SEQUENCE: 7

```
His Asn Asp Lys Arg Pro Ser
1               5
```

<210> SEQ ID NO 8
<211> LENGTH: 7
<212> TYPE: PRT
<213> ORGANISM: Homo sapiens

<400> SEQUENCE: 8

```
Tyr Asn Asp Lys Arg Pro Ser
1               5
```

<210> SEQ ID NO 9
<211> LENGTH: 10
<212> TYPE: PRT
<213> ORGANISM: Homo sapiens

<400> SEQUENCE: 9

```
Gly Ser Ala Asp Arg Ser Gly Ala Gly Ile
1               5                   10
```

<210> SEQ ID NO 10
<211> LENGTH: 129
<212> TYPE: PRT
<213> ORGANISM: Homo sapiens

<400> SEQUENCE: 10

```
Ala Val Thr Leu Asp Glu Ser Gly Gly Leu His Thr Pro Gly Gly
1               5                   10                  15

Gly Leu Ser Leu Val Cys Arg Ala Ser Gly Phe Thr Phe Ser Ser Tyr
                20                  25                  30

Ala Met Gln Trp Val Arg Gln Ala Pro Gly Lys Gly Leu Glu Trp Val
            35                  40                  45

Ala Gly Met Ser Asp Asp Gly Ser Trp Thr Asp Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Gly Ala Gly Thr Gly Tyr Cys Asp Asn Arg Ser Phe Gly Cys
            100                 105                 110
```

```
Ala Ser Thr Ile Asp Ala Trp Gly His Gly Thr Glu Val Ile Val Ser
            115                 120                 125
Ser

<210> SEQ ID NO 11
<211> LENGTH: 103
<212> TYPE: PRT
<213> ORGANISM: Homo sapiens

<400> SEQUENCE: 11

Ala Leu Thr Gln Pro Ser Ser Val Ser Ala Asn Leu Gly Glu Thr Val
1               5                   10                  15

Glu Ile Thr Cys Ser Gly Ser Ser Gly Ser Tyr Gly Trp Tyr Gln Gln
            20                  25                  30

Lys Ser Pro Gly Ser Ala Pro Val Thr Val Ile Tyr His Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
                85                  90                  95

Gly Thr Thr Leu Thr Val Leu
            100

<210> SEQ ID NO 12
<211> LENGTH: 129
<212> TYPE: PRT
<213> ORGANISM: Homo sapiens

<400> SEQUENCE: 12

Ala Val Thr Leu Asp Glu Ser Gly Gly Gly Leu Gln Thr Pro Gly Gly
1               5                   10                  15

Gly Leu Ser Leu Val Cys Arg Ala Ser Gly Phe Thr Met Thr Ser Tyr
            20                  25                  30

Ala Met Gln Trp Val Arg Gln Ala Pro Gly Lys Gly Leu Glu Trp Val
        35                  40                  45

Ala Gly Val Ser Asp Asp Gly Ser Trp Thr Gly Tyr Gly Ala Ala Val
    50                  55                  60

Gln Gly Arg Ala Thr Ile Ser Arg Asp Asn Gly Gln Ser Thr Val Arg
65                  70                  75                  80

Leu Leu Leu Asn Asn Leu Arg Ala Glu Asp Thr Ala Thr Tyr Tyr Cys
                85                  90                  95

Val Lys Gly Ala Gly Thr Gly Tyr Cys Asn Asn Arg Gly Phe Gly Cys
            100                 105                 110

Ala Ser Thr Ile Asp Ala Trp Gly His Gly Thr Glu Val Ile Val Ser
        115                 120                 125
Ser

<210> SEQ ID NO 13
<211> LENGTH: 103
<212> TYPE: PRT
<213> ORGANISM: Homo sapiens

<400> SEQUENCE: 13

Ala Leu Thr Gln Pro Ser Ser Val Ser Ala Asn Leu Gly Glu Thr Val
1               5                   10                  15
```

-continued

```
Glu Ile Thr Cys Ser Gly Ser Ser Ser Tyr Gly Trp Tyr Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
                85                  90                  95

Gly Thr Thr Leu Thr Val Leu
                100

<210> SEQ ID NO 14
<211> LENGTH: 250
<212> TYPE: PRT
<213> ORGANISM: Homo sapiens

<400> SEQUENCE: 14

Ala Leu Thr Gln Pro Ser Ser Val Ser Ala Asn Leu Gly Glu Thr Val
1               5                   10                  15

Glu Ile Thr Cys Ser Gly Ser Ser Gly Ser Tyr Gly Trp Tyr Gln Gln
                20                  25                  30

Lys Ser Pro Gly Ser Ala Pro Val Thr Val Ile Tyr His Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
                85                  90                  95

Gly Thr Thr Leu Thr Val Leu Gly Gln Ser Ser Arg Ser Ser Gly Gly
                100                 105                 110

Gly Gly Ser Ser Gly Gly Gly Ser Ala Val Thr Leu Asp Glu Ser
        115                 120                 125

Gly Gly Gly Leu His Thr Pro Gly Gly Leu Ser Leu Val Cys Arg
    130                 135                 140

Ala Ser Gly Phe Thr Phe Ser Ser Tyr Ala Met Gln Trp Val Arg Gln
145                 150                 155                 160

Ala Pro Gly Lys Gly Leu Glu Trp Val Ala Gly Met Ser Asp Asp Gly
                165                 170                 175

Ser Trp Thr Asp Tyr Gly Ala Ala Val Lys Gly Arg Ala Thr Ile Ser
            180                 185                 190

Arg Asp Asn Gly Gln Ser Thr Val Arg Leu Gln Leu Asn Asn Leu Arg
        195                 200                 205

Ala Glu Asp Thr Gly Thr Tyr Tyr Cys Ala Lys Gly Ala Gly Thr Gly
    210                 215                 220

Tyr Cys Asp Asn Arg Ser Phe Gly Cys Ala Ser Thr Ile Asp Ala Trp
225                 230                 235                 240

Gly His Gly Thr Glu Val Ile Val Ser Ser
                245                 250

<210> SEQ ID NO 15
<211> LENGTH: 239
<212> TYPE: PRT
<213> ORGANISM: Homo sapiens
```

```
<400> SEQUENCE: 15

Ala Leu Thr Gln Pro Ser Ser Val Ser Ala Asn Leu Gly Glu Thr Val
1               5                   10                  15

Glu Ile Thr Cys Ser Gly Ser Ser Gly Ser Tyr Gly Trp Tyr Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
            85                  90                  95

Gly Thr Thr Leu Thr Val Leu Gly Gln Ser Ser Arg Ser Ser Ala Val
            100                 105                 110

Thr Leu Asp Glu Ser Gly Gly Gly Leu Gln Thr Pro Gly Gly Gly Leu
            115                 120                 125

Ser Leu Val Cys Arg Ala Ser Gly Phe Thr Met Thr Ser Tyr Ala Met
            130                 135                 140

Gln Trp Val Arg Gln Ala Pro Gly Lys Gly Leu Glu Trp Val Ala Gly
145                 150                 155                 160

Val Ser Asp Asp Gly Ser Trp Thr Gly Tyr Gly Ala Ala Val Gln Gly
            165                 170                 175

Arg Ala Thr Ile Ser Arg Asp Asn Gly Gln Ser Thr Val Arg Leu Leu
            180                 185                 190

Leu Asn Asn Leu Arg Ala Glu Asp Thr Ala Thr Tyr Tyr Cys Val Lys
            195                 200                 205

Gly Ala Gly Thr Gly Tyr Cys Asn Asn Arg Gly Phe Gly Cys Ala Ser
            210                 215                 220

Thr Ile Asp Ala Trp Gly His Gly Thr Glu Val Ile Val Ser Ser
225                 230                 235
```